(12) United States Patent
Baratto et al.

(10) Patent No.: US 9,091,618 B1
(45) Date of Patent: Jul. 28, 2015

(54) GAS SAMPLING SYSTEM

(75) Inventors: Joseph Michael Baratto, Seattle, WA (US); Cheryl Bick, Seattle, WA (US); James D. Edgerton, Renton, WA (US)

(73) Assignee: THE BOEING COMPANY, Chicago, IL (US)

( * ) Notice: Subject to any disclaimer, the term of this patent is extended or adjusted under 35 U.S.C. 154(b) by 401 days.

(21) Appl. No.: 13/592,965

(22) Filed: Aug. 23, 2012

(51) Int. Cl.
*G01N 1/20* (2006.01)

(52) U.S. Cl.
CPC .................................. *G01N 1/2035* (2013.01)

(58) Field of Classification Search
CPC ........................................................ B23B 27/00
USPC ............. 700/198, 197, 30, 31, 118, 119, 204; 29/848, 849, 856, 858; 264/40.1, 40.5, 264/325, 236, 40.2, 40.6; 426/512, 513, 426/517; 425/135, 143; 364/469, 473, 476, 364/477; 324/663; 156/64, 87; 73/863, 864
See application file for complete search history.

(56) References Cited

U.S. PATENT DOCUMENTS

| | | | |
|---|---|---|---|
| 3,666,600 A * | 5/1972 | Yoshino | .......................... 156/382 |
| 4,442,353 A | 4/1984 | Baubron | |
| 5,219,498 A | 6/1993 | Keller | |
| 5,345,397 A * | 9/1994 | Handel et al. | .................. 700/274 |
| 5,525,799 A | 6/1996 | Andresen | |
| 5,736,654 A * | 4/1998 | Dubois | ....................... 73/863.84 |
| 6,077,350 A * | 6/2000 | Morton et al. | .................... 118/58 |

OTHER PUBLICATIONS

Berenberg, Improving Autoclave Performance_Precision process controls optimize quality of autoclave-cured parts, Mar. 2003, High-Performance Composites, Gardner Business Media.*
Upadhya et al., Autoclaves for Aerospace Applications: Issues and Challenges, Apr. 2011, International Journal of Aerospace Engineering vol. 2011, Article ID 985871, p. 1-12.*
"Hapsite ER Chemical Identification System," INFICON, copyright 2012, 2 Pages, accessed Jul. 31, 2012 http://www.inficonemergencyresponse.com/en/hapsite_er//index.html.

* cited by examiner

*Primary Examiner* — Hezron E Williams
*Assistant Examiner* — Truong Phan
(74) *Attorney, Agent, or Firm* — Yee & Associates, P.C.

(57) ABSTRACT

A method and apparatus comprising a sample collection structure having a chamber and an interface for the sample collection structure. The interface is configured to be connected to a curing system and a vacuum source. The curing system is configured to cure a composite part. The vacuum source is configured to create a vacuum in the curing system. The interface is further configured to collect a sample of a gas from the curing system in the chamber. The interface is further configured to send the sample of the gas collected in the chamber to an analyzer.

19 Claims, 14 Drawing Sheets

GAS SAMPLING SYSTEM

BACKGROUND INFORMATION

1. Field

The present disclosure relates generally to manufacturing composite parts and, in particular, to a method and apparatus for monitoring gas generated during curing of a composite part. Still more particularly, the present disclosure relates to collecting a sample of gas generated during curing of a composite part under a vacuum.

2. Background

Aircraft are being designed and manufactured with greater and greater percentages of composite materials. Composite materials are used in aircraft to decrease the weight of the aircraft. This decreased weight improves performance features such as payload capacity and fuel efficiency. Further, composite materials provide longer service life for various components in an aircraft.

Composite materials may be tough, lightweight materials created by combining two or more functional components. For example, a composite material may include reinforcing fibers bound in a polymer resin matrix. The fibers may be unidirectional or may take the form of a woven cloth or fabric. The fibers and resins may be arranged and cured to form a composite part.

Using composite materials to create composite parts may allow for portions of an aircraft to be manufactured in larger pieces or sections. For example, a fuselage in an aircraft may be created in cylindrical sections and later joined to form the fuselage of the aircraft. Other examples include, without limitation, wing sections joined to form a wing or stabilizer sections joined to form a stabilizer.

In manufacturing composite parts, layers of composite material may be laid up on a tool. The layers of composite material may be comprised of fibers in sheets. These sheets may take the form of, for example, without limitation, fabrics, tape, tows, or other suitable configurations of sheets. In some cases, resin may be infused or pre-impregnated into the sheets. These types of sheets are commonly referred to as prepreg.

The different layers of prepreg may be laid up in different orientations and different numbers of layers may be used depending on the desired thickness of composite part being manufactured. These layers may be laid up by hand or using automated equipment such as a tape laminating machine or a fiber placement system.

After the different layers have been laid up on the tool, the layers may be consolidated and cured upon exposure to temperature and pressure, thus forming the final composite part. The curing may be performed in an oven. A composite part in the oven may be placed under a vacuum. For example, a composite part may be covered with a bag. A vacuum may be applied to the bag while the part is heated in the oven. The vacuum with the bag may apply pressure to the composite part.

After the composite part has been cured, the composite part may be inspected to determine whether inconsistencies are present. For example, ultrasound inspection, x-ray inspection, eddy current inspection, and other techniques may be used to determine whether inconsistencies such as delamination, debonding, or other undesired inconsistencies are present within the composite part.

If inconsistencies are identified in the composite part, an analysis may be performed to determine the cause. The result of the analysis may lead to changes in materials used, orientation of layers, heating times, temperatures, and other parameters for manufacturing the composite part.

This process, however, may be more time-consuming than desired. Depending on the inconsistencies identified, the composite part may be reworked or may need to be discarded. As a result, in some cases, the analysis may require a new composite part to be formed. Forming the new composite part may take more time and expense than desired.

Therefore, it would be desirable to have a method and apparatus that takes into account at least some of the issues discussed above, as well as other possible issues.

SUMMARY

In one illustrative embodiment, an apparatus comprises a sample collection structure having a chamber and an interface for the sample collection structure. The interface is configured to be connected to a curing system and a vacuum source. The curing system is configured to cure a composite part. The vacuum source is configured to create a vacuum in the curing system. The interface is further configured to collect a sample of a gas from the curing system in the chamber. The interface is further configured to send the sample of the gas collected in the chamber to an analyzer.

In another illustrative embodiment, an apparatus comprises a sample collection structure and valve system. The sample collection structure has a chamber, a first input port, a first output port, a second input port, and a second output port. The first input port is configured to be connected to a curing system for curing layers of composite material for a composite part. The first output port is configured to be connected to a vacuum source. The second input port is configured to be connected to a gas source. The second output port is configured to be connected to an analyzer. A valve system is associated with the first input port, the first output port, the second input port, and the second output port. The valve system is configured to collect a sample of a gas from the curing system in the chamber. The valve system is further configured to send the sample of the gas collected in the chamber to the analyzer.

In yet another illustrative embodiment, a method for collecting a sample of a gas is present. The sample of the gas flowing from a curing system to a vacuum source is collected into a chamber of a sample collection structure while the gas continues to flow in a manner that maintains a desired level of vacuum in the curing system. The gas is generated from curing layers of composite material for a composite part in the curing system. The sample of the gas is sent to an analyzer with a level of pressure used by the analyzer.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

Figure 1:
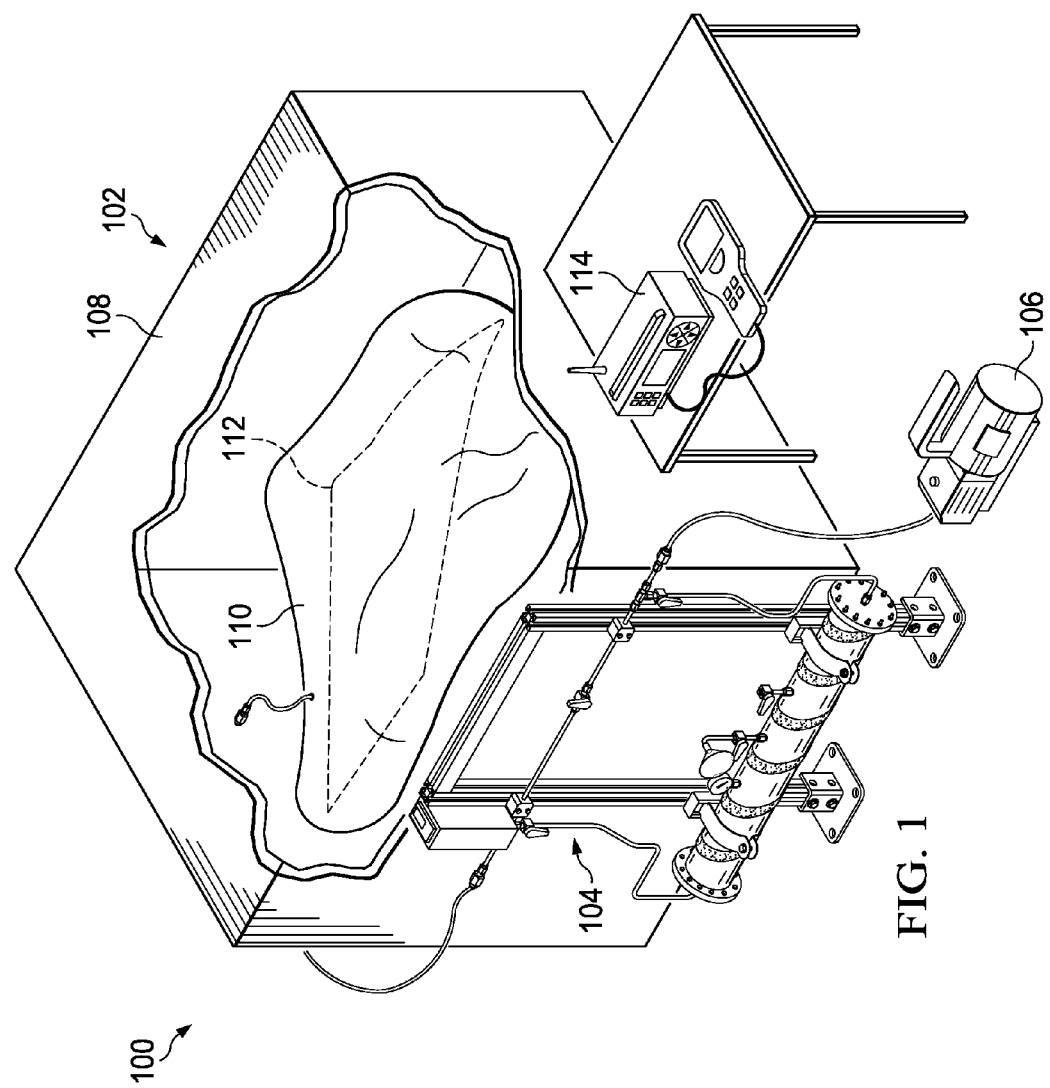
FIG. 1 is an illustration of a composite part manufacturing environment in accordance with an illustrative embodiment.

The illustrative embodiments recognize and take into account one or more different considerations. For example, the illustrative embodiments recognize and take into account that a vacuum may be applied to a composite part in an autoclave, in a vacuum bag, or in other situations during curing of the composite part. The illustrative embodiments recognize and take into account that collecting and analyzing samples of gases generated during the curing process may provide information needed to make adjustments in the curing process. These adjustments may be made in subsequent curing of similar parts.

Further, the illustrative embodiments also recognize and take into account that monitoring gases generated during the curing process for a composite part may be used to determine whether the composite part will have a desired quality when completed. The illustrative embodiments recognize and take into account that the detection of gases, the amount of gases generated, when particular gases are generated, or some combination thereof during the curing of a composite part may indicate whether the composite part will have a desired quality.

The illustrative embodiments also recognize and take into account that by monitoring gases generated during a curing process for a composite part, improved quality of composite parts may be obtained. Adjustments may be made to the curing process based on an identification of gases generated during the curing process such that cured composite parts may have a desired quality.

The illustrative embodiments also recognize and take into account that, in some cases, adjustments may be made prior to the composite part being completely cured. For example, when certain components are no longer present in a gas sample, a particular temperature used to cure the layers of composite material for the composite part may be changed to another temperature. Thus, this change may be made when the components are no longer detected as opposed to waiting for a particular period of time to elapse. As a result, curing times for a composite part may be reduced.

The illustrative embodiments also recognize and take into account that an analysis of the gas generated during the curing of a composite part may be performed using a system, such as a gas chromatography mass spectrometer, to identify the components in the gas. Further, the illustrative embodiments also recognize and take into account that knowledge of the components in a gas may be used to make adjustments to a composite part currently being cured or to subsequent composite parts that are processed.

Additionally, the illustrative embodiments recognize and take into account that knowledge of the different components in the gas at different temperatures during a curing process may be employed to maximize the parameters used for curing a composite part. In this manner, part qualities may be improved, curing times may be reduced, and other benefits may be realized. In other words, a sample of the gas generated during the curing of a composite part may be used to make adjustments to a curing profile in a manner that increases part quality, production rate, and provides other benefits.

The illustrative embodiments also recognize and take into account that sampling a gas at the vacuum source may not provide a desired level of quality for the sample of the gas. The gas, when reaching the vacuum source, may be subjected to filters, lines with contaminants, and other undesirable conditions. In other words, the sample of gas taken at the vacuum source may not adequately reflect the components of the gas generated during the curing process.

The illustrative embodiments also recognize and take into account that the monitoring of gases may also be useful during the processing of other types of parts or materials other than composite parts. The illustrative embodiments recognize and take into account that the monitoring of gases generated during the processing of a part under a vacuum may be useful to identify information about other types of parts or materials.

Thus, the illustrative embodiments provide a method and apparatus for collecting a sample of the gas. In one illustrative embodiment, an apparatus comprises a sample collection structure having a chamber and an interface for the sample collection structure.

The interface is configured to be connected to a curing system. The curing system is configured to cure a composite part. A vacuum source is configured to create a vacuum in an oven. In these illustrative examples, a vacuum may be applied to the composite part using a vacuum bag or other structure in the curing system. The interface is also configured to collect a sample of the gas from the oven in the chamber and send the sample of the gas collected in the chamber to an analyzer.

With reference now to the figures and, in particular, with reference to FIG. 1, an illustration of a composite part manufacturing environment is depicted in accordance with an illustrative embodiment. In this example, composite part manufacturing environment 100 includes curing system 102, gas sampling system 104, and vacuum source 106.

As depicted, curing system 102 includes oven 108 and vacuum bag 110. In this illustrative example, an exposed view of oven 108 is shown such that horizontal stabilizer 112 within oven 108 can be seen. Horizontal stabilizer 112 is a composite part in his illustrative example. Horizontal stabilizer 112 is formed from layers of composite material. In this example, horizontal stabilizer 112 is shown in an uncured state.

Oven 108 may heat horizontal stabilizer 112 to various temperatures during different periods of time in the curing process. The different temperatures over different periods of time in the curing process may be referred to as a curing profile.

As horizontal stabilizer 112 is heated within oven 108, vacuum source 106 may draw a vacuum on horizontal stabilizer 112. In particular, vacuum source 106 may draw a vacuum through vacuum bag 110 placed over horizontal stabilizer 112. The vacuum drawn on vacuum bag 110 results in pressure being applied to horizontal stabilizer 112 while being heated within oven 108.

As horizontal stabilizer 112 is cured, a gas may be generated in vacuum bag 110. This gas may be drawn out of oven 108 by vacuum source 106.

As depicted, gas sampling system 104 is located between oven 108 and vacuum source 106. In these illustrative examples, gas sampling system 104 is configured to collect a sample of the gas drawn from the vacuum in oven 108 by vacuum source 106.

In this illustrative example, the sample collected by gas sampling system 104 may be sent to analyzer 114. Analyzer 114 is configured to identify components in the sample of the gas. The identification of the components in the sample of the gas may be used to make adjustments to the process for curing horizontal stabilizer 112 in oven 108.

In other illustrative examples, the identification of the components in the sample of the gas from oven 108 also may be used to make changes to layers of composite material used to form horizontal stabilizer 112. These changes may include, for example, without limitation, changes in the types of layers, resin, orientation of layers, number of layers, and other suitable changes to the layers of composite material in horizontal stabilizer 112.

The illustration of composite part manufacturing environment 100 is only an illustration of one manner in which composite part manufacturing environment 100 may be implemented with gas sampling system 104. Gas sampling system 104 may be used with other components in addition to or in place of the ones illustrated. Additionally, in some illustrative examples, oven 108 may also apply pressure to horizontal stabilizer 112. For example, oven 108 may take the form of an autoclave. In another illustrative example, an open air heater may be used with vacuum bag 110 to provide heat and pressure for curing horizontal stabilizer 112.

Figure 2:
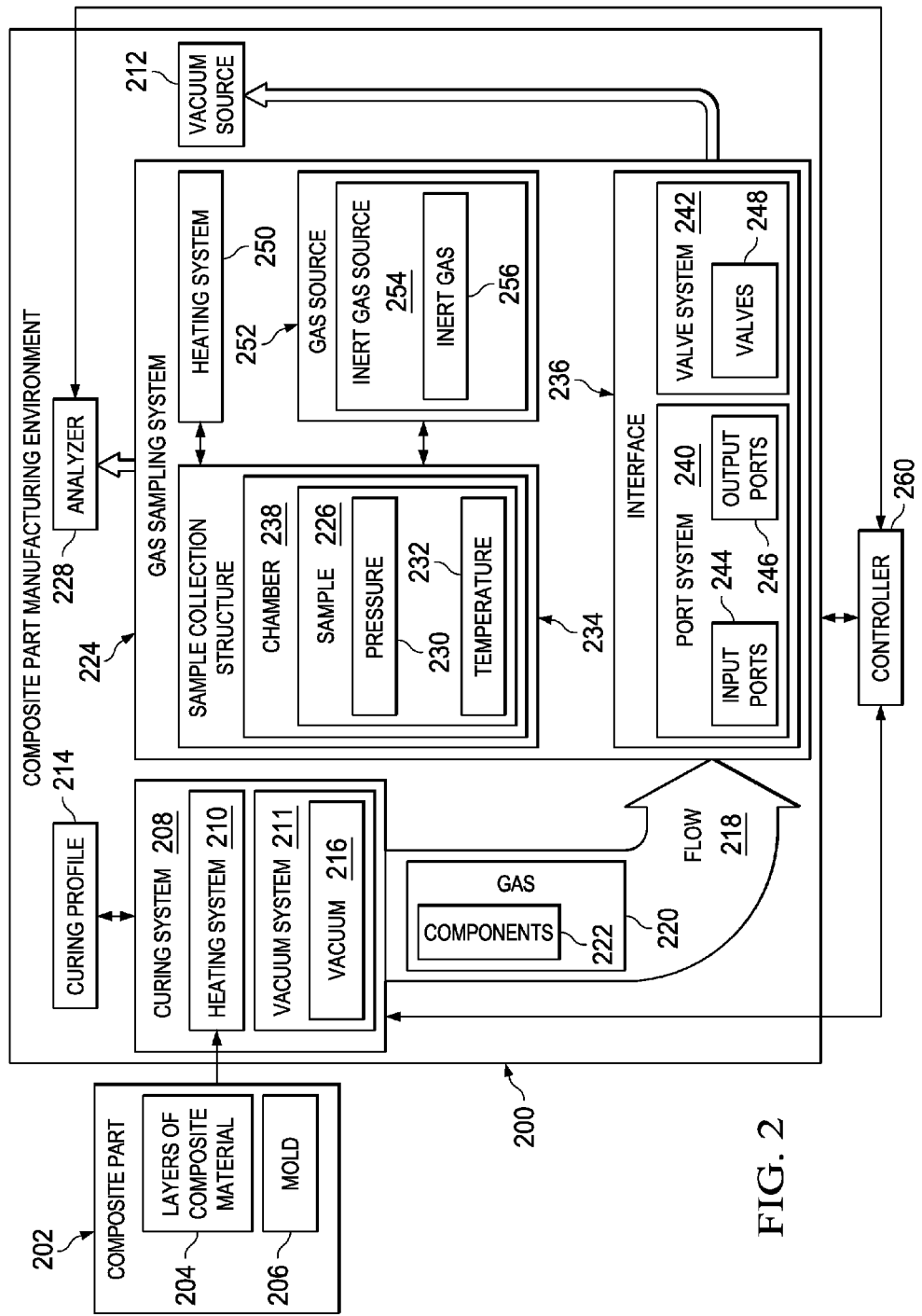
FIG. 2 is an illustration of a block diagram of a composite part manufacturing environment in accordance with an illustrative embodiment.

Turning now to FIG. 2, an illustration of a block diagram of a composite part manufacturing environment is depicted in accordance with an illustrative embodiment. Composite part manufacturing environment 100 is an example of one implementation for composite part manufacturing environment 200 shown in block form in FIG. 2.

In this illustrative example, composite part manufacturing environment 200 may be used to manufacture composite part 202. Composite part 202 may be, for example, horizontal stabilizer 112 in FIG. 1. Of course, composite part 202 may take other forms. For example, without limitation, composite part 202 may take the form of a panel, a stringer, a horizontal stabilizer, a wing, a fuselage barrel, a monument, a chair frame, and other suitable types of composite parts.

In this illustrative example, layers of composite material 204 may be laid up on mold 206 to form composite part 202. At this point, composite part 202 is in an uncured form. Layers of composite material 204 laid up on mold 206 to form composite part 202 may be cured using curing system 208 to form composite part 202 in a cured form that is ready for inspection and use.

In this illustrative example, curing system 208 includes heating system 210 and vacuum system 211. In this illustrative example, heating system 210 may take various forms. For example, without limitation, heating system 210 may be an oven, an oven that also applies pressure such as an autoclave, an open air heater, or some other suitable type of heating device configured to generate heat for curing a composite part.

Vacuum system 211 is configured to draw vacuum 216 on composite part 202 when connected to vacuum source 212. As used herein, a first component "connected to" a second component means that the first component can be connected directly or indirectly to the second component. In other words, additional components may be present between the first component and the second component.

The first component is considered to be indirectly connected to the second component when one or more additional components are present between the two components. When the first component is directly connected to the second component, no additional components are present between the two components.

In this illustrative example, vacuum system 211 is indirectly connected to vacuum source 212 through a connection system. This connection system may be any connection system that directs airflow toward vacuum source 212. For example, this connection system may be a piping system.

As depicted, vacuum system 211 may take a number of different forms. For example, vacuum system 211 may be a vacuum bag that covers part or all of composite part 202. In other illustrative examples, vacuum system 211 may be a structure configured to generate a vacuum on part or all of composite part 202 when connected to vacuum source 212.

Curing system 208 is configured to heat composite part 202 to different temperatures for different periods of time based on curing profile 214. In this illustrative example, vacuum source 212 is configured to draw vacuum 216 in curing system 208. In particular, vacuum 216 may be drawn on composite part 202 in curing system 208.

In this illustrative example, as vacuum 216 is generated in curing system 208, flow 218 of gas 220 may occur during the curing of layers of composite material 204 in composite part 202. In particular, gas 220 may be generated when layers of composite material 204 in composite part 202 are heated by heating system 210.

Gas 220 may be generated during heating of layers of composite material 204 and may have components 222. Components 222 in gas 220 may be different types of gases that result in a cross-linking cure reaction within layers of composite material 204. Different types of gases and different amounts of gases may be present in gas 220 during different periods of time in the curing process. These different gases may be caused by the different reactions occurring between materials in layers of composite material 204.

As depicted, components 222 in gas 220 may include, for example, at least one of carbon dioxide, acetone, ethyl acetate, propane, butane, silane, pentanedioic acid, dimethyl ester, and other suitable components. Components 222 in gas 220 may change during different times during the curing of composite part 202. For example, as the temperature changes in curing system 208, components 222 in gas 220 may change. These temperature changes may cause or initiate different types of reactions within layers of composite material 204.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C, or item B and item C.

In this illustrative example, gas sampling system 224 is configured to collect sample 226 of gas 220 from flow 218 of gas 220. In these illustrative examples, gas sampling system 224 may be located between curing system 208 and vacuum source 212. In particular, gas sampling system 224 may collect sample 226 from flow 218 of gas 220 prior to gas 220 reaching vacuum source 212. Gas sampling system 224 may be configured to avoid introducing contaminants into sample 226.

In this illustrative example, gas sampling system 224 is configured to send sample 226 to analyzer 228. Analyzer 228 is configured to identify components 222 in sample 226 of gas 220.

With the analysis made by analyzer 228, if components 222 in sample 226 of gas 220 has a desired profile, then a conclusion may be made that desired reactions have occurred within composite part 202 at a desired time. In other words, if components 222 in gas 220 are expected components at a particular time, then composite part 202 may have a desired quality. This monitoring of gas 220 may be performed in addition to or in place of an inspection of composite part 202 after being cured by curing system 208.

Further, with the identification of components 222, changes may be made to at least one of curing profile 214, layers of composite material 204, and other parameters relating to the manufacture of composite part 202 if components 222 in sample 226 of gas 220 are not expected components. In this manner, improvements may be made to a curing process for composite part 202 through the monitoring of gas 220.

In these illustrative examples, gas sampling system 224 is configured to collect sample 226 in a manner that allows vacuum source 212 to maintain a desired level of vacuum 216 in curing system 208. In other words, vacuum 216 applied to layers of composite material 204 may be maintained at a desired level while gas sampling system 224 collects sample 226.

Additionally, gas sampling system 224 also may send sample 226 to analyzer 228 with a desired level of pressure 230. The desired level of pressure 230 may be a level of pressure 230 that is normally used by analyzer 228. The pressure in sample 226 collected by gas sampling system 224 from curing system 208 is lower than one atmosphere.

In these illustrative examples, analyzer 228 may expect pressure 230 to be one atmosphere when performing an analysis of sample 226. If pressure 230 is not the expected level of pressure for analyzer 228, analyzer 228 may reject the sample, generate inaccurate results, or some combination thereof.

Additionally, gas sampling system 224 also may send sample 226 to analyzer 228 with a desired level of temperature 232. Temperature 232 may be substantially the same temperature as the temperature in curing system 208. When collecting a sample of gas 220, maintaining a desired temperature may prevent additional chemical reactions from occurring inside sample collection structure 234.

For example, if temperature 232 inside sample collection structure 234 is not substantially the same temperature as the temperature of curing system 208, components 222 in gas 220 may drop out of the mobile gas phase. These changes to components 222 in gas 220 may not provide an accurate sample to analyzer 228. In other words, keeping temperature 232 substantially the same as the temperature inside curing system 208 maintains the integrity of the sample.

As a result, more accurate identifications of components 222 in gas 220 may occur. In this manner, the monitoring of gas 220 may be used to determine whether composite part 202 has a desired quality.

In this illustrative example, gas sampling system 224 includes sample collection structure 234 and interface 236. Sample collection structure 234 has chamber 238. Sample 226 is collected within chamber 238 of gas sampling system 224 in these illustrative examples.

Interface 236 is configured to be connected to curing system 208 and vacuum source 212. In particular, interface 236 may be connected to vacuum system 211 in curing system 208. Additionally, interface 236 also may be connected to analyzer 228.

In this illustrative example, interface 236 is configured to collect sample 226 of gas 220 from curing system 208 and send sample 226 of gas 220 collected in chamber 238 to analyzer 228. As depicted, interface 236 includes port system 240 and valve system 242. Port system 240 provides connections between chamber 238 in sample collection structure 234, curing system 208, and vacuum source 212.

Port system 240 includes input ports 244 and output ports 246. Input ports 244 are configured to allow for flow 218 of gas 220 into chamber 238 while output ports 246 are configured to allow for flow 218 of gas 220 out of chamber 238. As depicted, valve system 242 includes valves 248 configured to control flow 218 of gas 220 through input ports 244 and output ports 246 in port system 240.

Gas sampling system 224 may also include heating system 250. Heating system 250 is configured to maintain sample 226 of gas 220 with temperature 232 at a desired level.

Additionally, gas sampling system 224 also may include gas source 252. Gas source 252 may be inert gas source 254. Inert gas source 254 may be used to supply inert gas 256 to chamber 238 in a manner that adjusts pressure 230 to a desired level for use in analyzer 228.

Controller 260 is configured to control the operation of interface 236 in these illustrative examples. Controller 260 also may control the operation of curing system 208, vacuum source 212, and analyzer 228. In these illustrative examples, controller 260 may take the form of a computer system in which one or more computers may be present.

The illustration of composite part manufacturing environment 200 in FIG. 2 is not meant to imply physical or architectural limitations to the manner in which an illustrative embodiment may be implemented. For example, other illustrative embodiments may be applied to other types of manufacturing environments.

In these illustrative examples, gas sampling system 224 may be applied to sampling gas during the processing of any part or material that may generate gas. In particular, when the processing of a part involves reactions that generate different types of gases, those gases may be collected using gas sampling system 224 for analysis. For example, gas sampling system 224 may be used to sample gases generated during the manufacturing of printed circuit boards, semiconductor circuits, and other types of parts.

In other illustrative examples, gas sampling system 224 may even be used in a manufacturing environment in which a heating system is not used to process a part. If chemical reactions occur that generate a gas with different components, gas sampling system 224 may be implemented to sample the gas for analysis.

Figure 3:
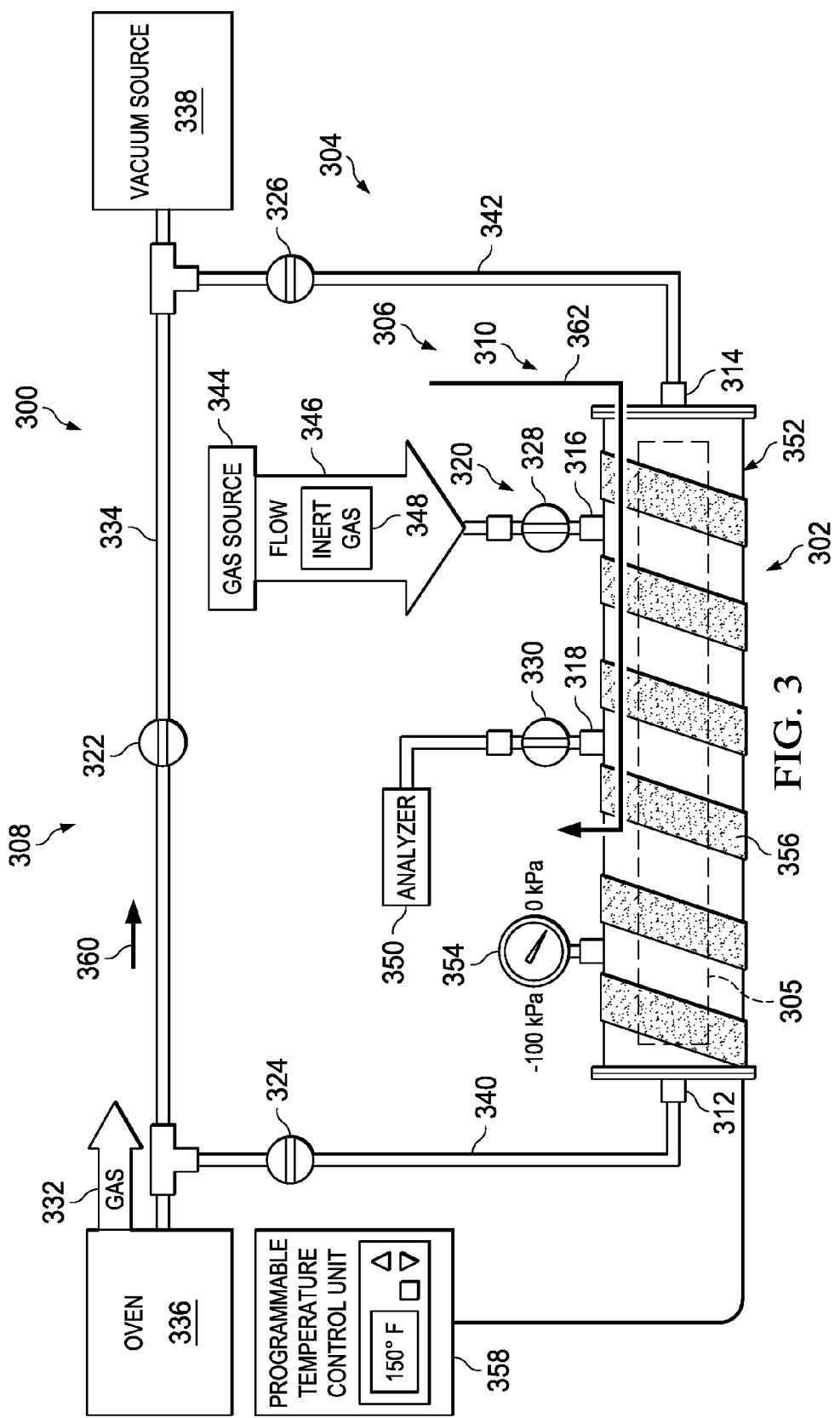
FIGS. 3-10 are illustrations of a collection of a gas sample using a gas sampling system in accordance with an illustrative embodiment.

Turning now to FIGS. 3-10, illustrations of a collection of a gas sample using a gas sampling system is depicted in accordance with an illustrative embodiment. A diagrammatic view of gas sampling system 300 is illustrated in FIG. 3. As depicted, gas sampling system 300 is an example of one implementation for gas sampling system 224 in FIG. 2.

As depicted, gas sampling system 300 includes sample collection structure 302 and interface 304. Sample collection structure 302 has chamber 305 located within sample collection structure 302. Interface 304 is comprised of port system 306 and valve system 308.

As depicted, ports 310 in port system 306 include first input port 312, first output port 314, second input port 316, and second output port 318. Valves 320 in valve system 308 include main line valve 322, first input valve 324, first output valve 326, second input valve 328, and second output valve 330.

In these illustrative examples, gas 332 originates in oven 336. Gas 332 flows into interface 304.

Main line valve 322 controls the flow of gas 332 from oven 336 through main line 334 to vacuum source 338. In particular, gas 332 may flow from a vacuum bag or other vacuum system connected to main line 334 in oven 336 when a vacuum is drawn by vacuum source 338 through main line 334.

In these illustrative examples, first input port 312 is connected to oven 336 through line 340 which is connected to main line 334. First input valve 324 controls the flow of gas 332 into first input port 312. As depicted, first output port 314 is connected to line 342 which is connected to main line 334.

Second input port 316 is connected to gas source 344. Second input valve 328 is configured to control flow 346 of inert gas 348 into sample collection structure 302. Second output port 318 is connected to analyzer 350. Second output valve 330 is configured to control the flow of a sample of gas 332 in chamber 305 to analyzer 350.

In this illustrative example, main line valve 322 is located between the connection of line 340 to main line 334 and line 342 to main line 334. First output valve 326 controls the flow of gas 332 to main line 334.

Additionally, gas sampling system 300 also may include heating system 352 and pressure sensor 354. Heating system 352 includes heating elements 356 and temperature control unit 358. Heating elements 356 are positioned around sample collection structure 302. Temperature control unit 358 may maintain a sample of gas 332 in chamber 305 at a desired temperature. In this illustrative example, the temperature is shown as about 150 degrees Fahrenheit. Of course other temperatures may be selected. The temperature may be selected to match the temperature in oven 336. As a result, temperature control unit 358 may change the temperature as oven 336 changes temperature in these illustrative examples.

In this illustrative example, pressure sensor 354 takes the form of a gauge. In other illustrative examples, pressure sensor 354 may be a sensor that sends data to a computer system or other type of controller.

In this illustrative example, interface 304 is configured to set up gas sampling system 300 for collecting a sample of gas 332. As depicted, main line valve 322 is in an open position. First input valve 324 and first output valve 326 are in a closed position. As a result, gas 332 flows from oven 336 in the direction of arrow 360 through main line 334 to vacuum source 338. Gas 332 does not flow into chamber 305.

Further, second input valve 328 and second output valve 330 are in an open position. In this position, inert gas 348 may be sent into and through chamber 305 in sample collection structure 302 to flow out of second output port 318 as indicated by arrow 362.

This flow of inert gas 348 may occur for some period of time to flush out or remove other gases that may be present in chamber 305. In this manner, contaminants or residual gases from prior samples may be removed from chamber 305. Chamber 305 may be pressurized with inert gas 348. Pressure sensor 354 may reflect this pressurization with a reading of about 0 kpa.

Figure 4:
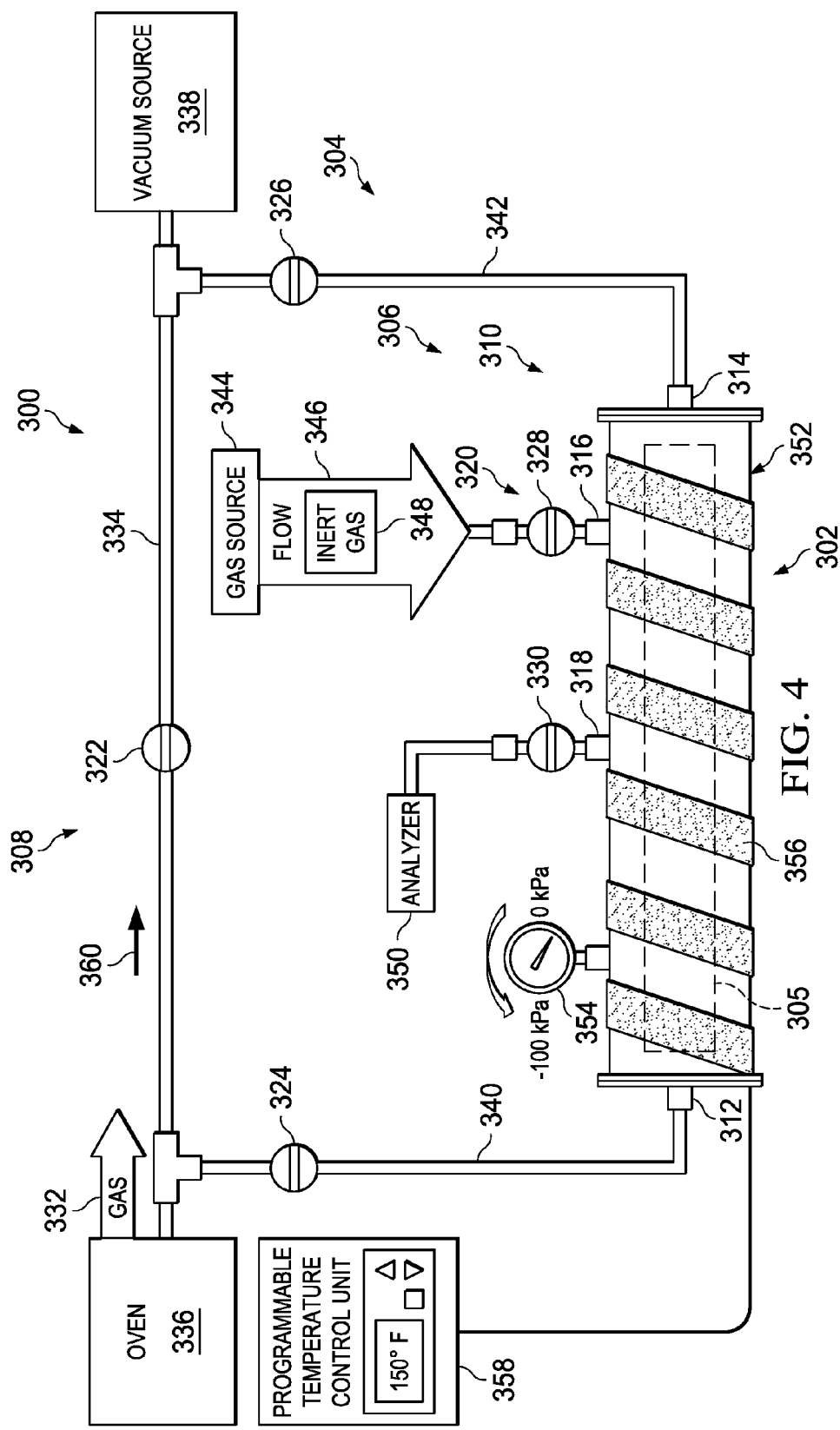

In FIG. 4, an illustration of another configuration of an interface for collecting a sample of gas is depicted in accordance with an illustrative embodiment. In this configuration of gas sampling system 300, second input valve 328 and second output valve 330 are placed into a closed position. In this configuration of gas sampling system 300, the flow of gas 332 only travels through main line 334 in the direction of arrow 360 from oven 336 to vacuum source 338. Inert gas 348 no longer flows through chamber 305.

As depicted, the flow of gas 332 is the normal flow of gas from oven 336 to vacuum source 338 in the process of curing a composite part. In this configuration, monitoring may be performed for temperatures where samples of gas are to be collected. In other illustrative examples, samples of gas may be gathered at different periods of time in addition to or in place of different temperatures.

Figure 5:
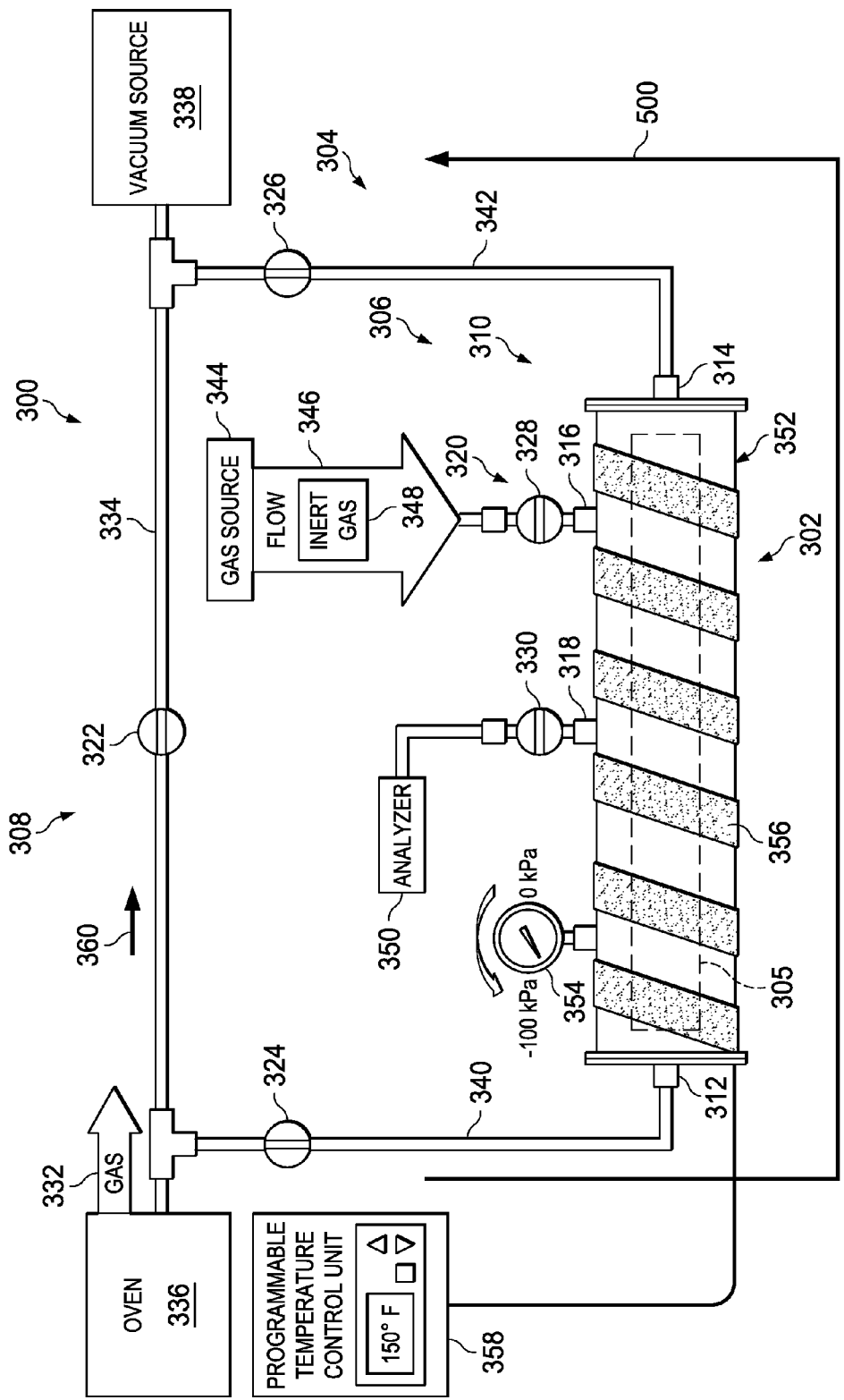

Turning now to FIG. 5, an illustration of a change in the configuration of an interface for collecting a sample of gas is depicted in accordance with an illustrative embodiment. In this figure, first input valve 324 and first output valve 326 are placed into an open position. In this position, gas 332 still flows in the direction of arrow 360. Additionally, gas 332 also flows into chamber 305, through chamber 305, and out of chamber 305 to main line 334 in the direction of arrow 500.

In this configuration, a vacuum is also drawn in chamber 305 in sample collection structure 302 by vacuum source 338. Thus, a vacuum is present in both oven 336 and chamber 305. The presence of the vacuum in chamber 305 may be shown on pressure sensor 354. In this illustrative example, pressure sensor 354 indicates that the pressure is about −100 kPa.

Figure 6:
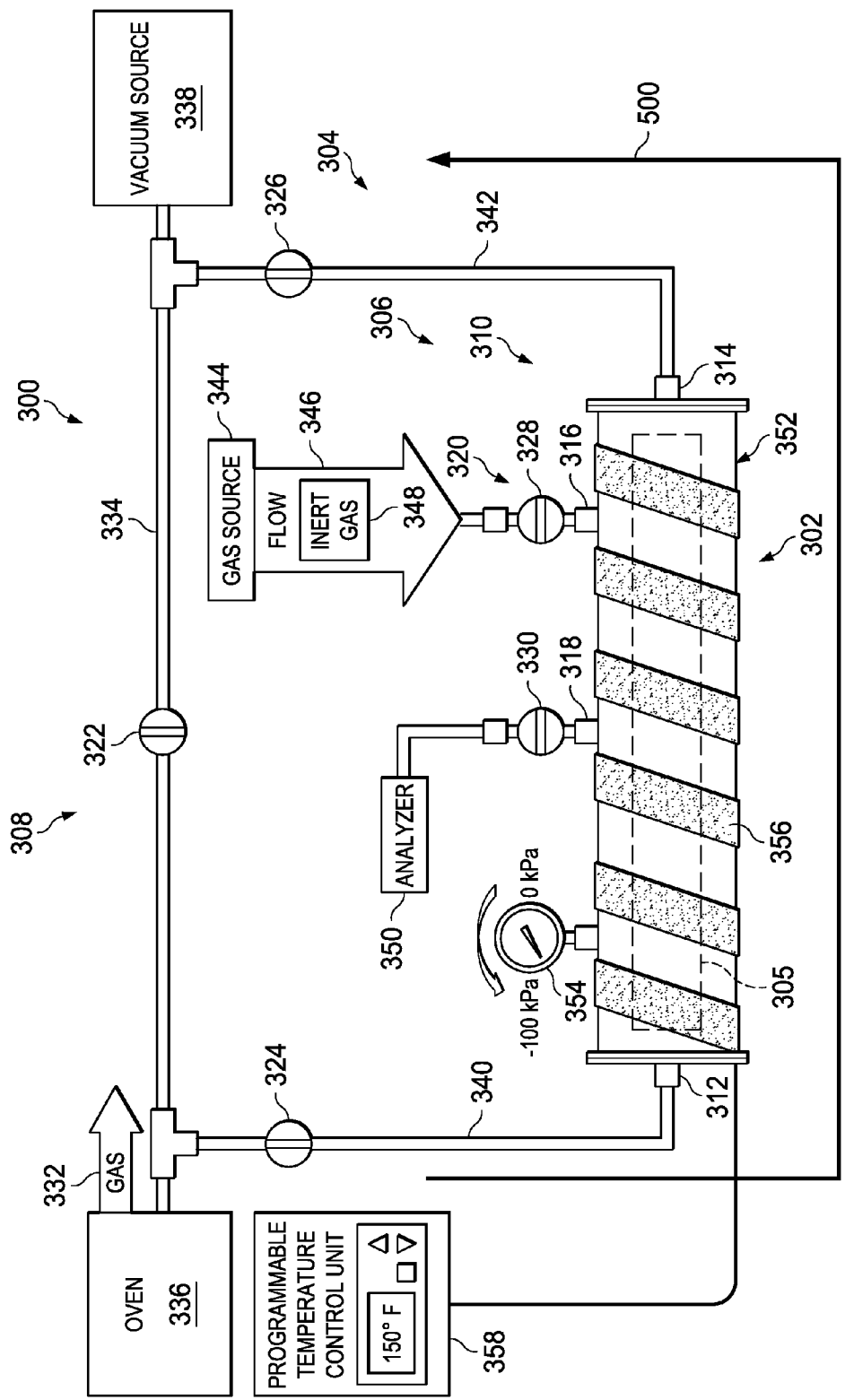

Turning now to FIG. 6, an illustration of a change in configuration of an interface for collecting a sample of gas is depicted in accordance with an illustrative embodiment. In this illustration, main line valve 322 is placed into a closed position. As a result, gas 332 no longer flows from oven 336 to vacuum source 338 through main line 334. Instead, gas 332 flows from main line 334 into line 340. Gas 332 flows from line 340 into chamber 305, through chamber 305, and out of chamber 305. Gas 332 flowing out of chamber 305 flows through line 342 to main line 334. This flow of gas 332 is shown by arrow 500.

In this configuration, all of gas 332 flows through chamber 305. This flow of gas 332 may occur for a period of time. This period of time may be, for example, from about two minutes to about three minutes. The selection of the amount of time for this flow may be a time in which a sufficient amount of gas 332 may be present in the flow through chamber 305 for sample collection of gas 332.

Figure 7:
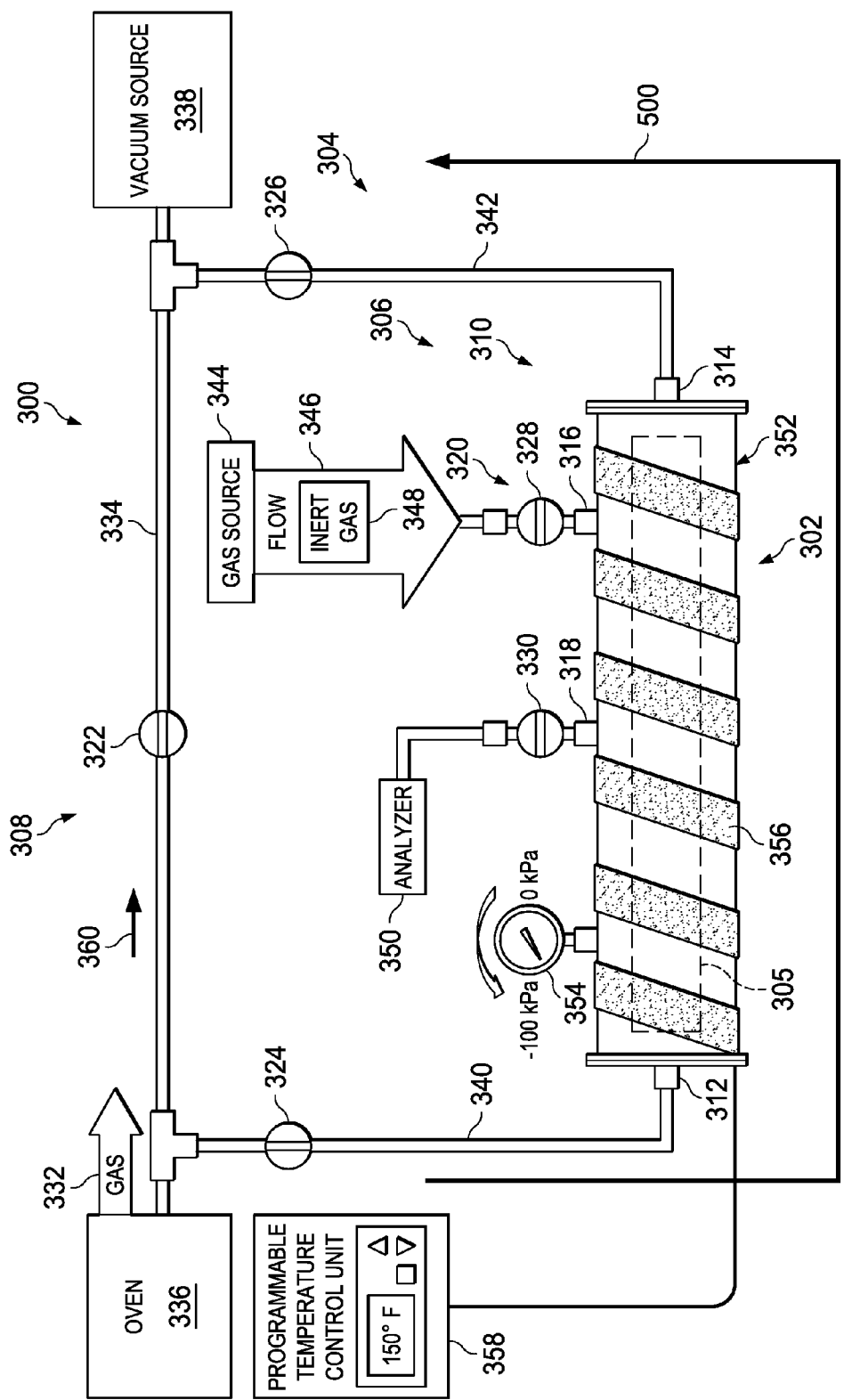

Turning now to FIG. 7, an illustration of another configuration of an interface for collecting a sample of gas is depicted in accordance with an illustrative embodiment. In this figure, main line valve 322 is placed into an open position such that gas 332 again flows through main line 334 as shown by arrow 360 in addition to flowing through chamber 305 as shown by arrow 500.

Figure 8:
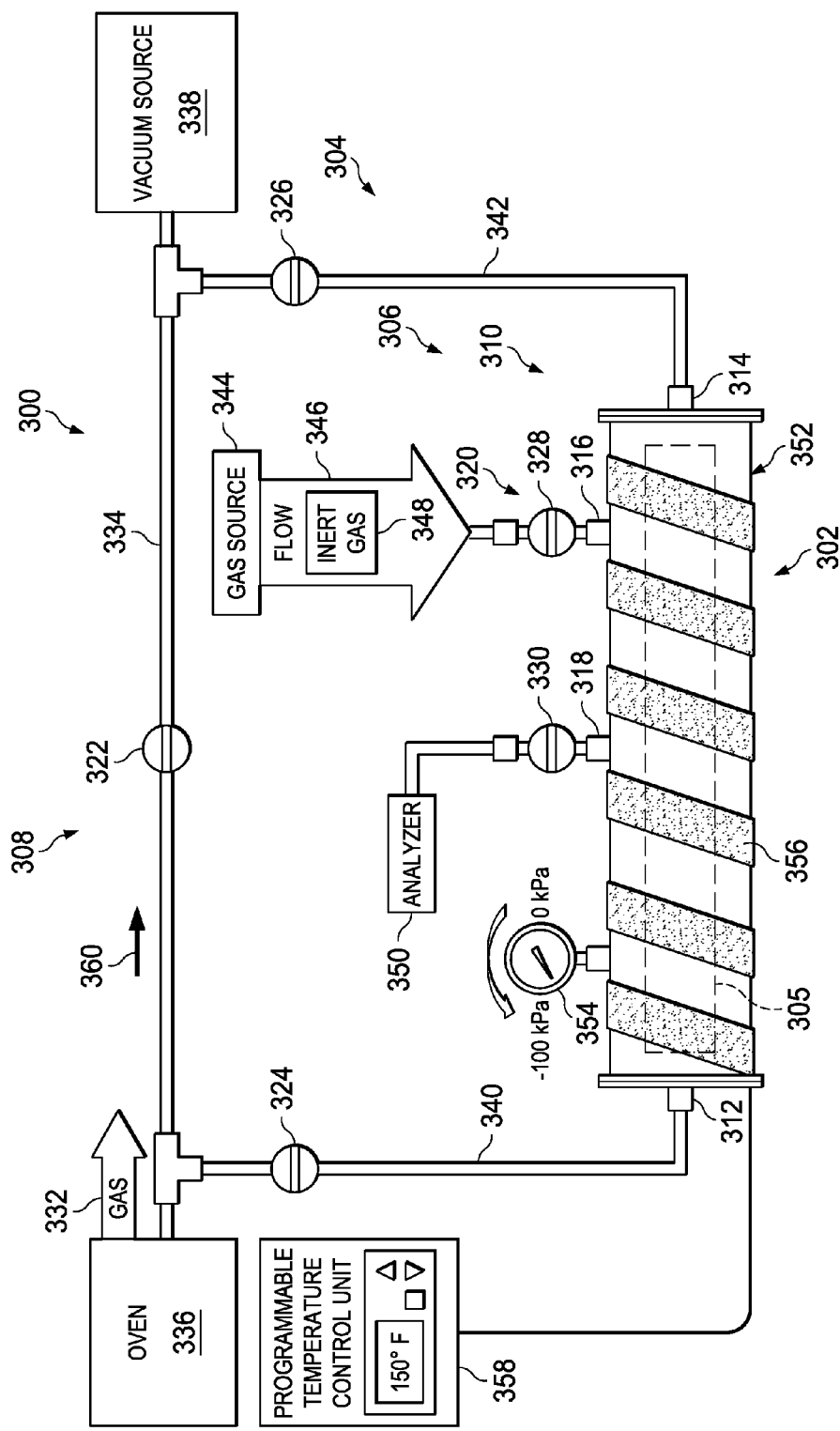

Turning now to FIG. 8, an illustration of another configuration of an interface for collecting a sample of gas is depicted in accordance with an illustrative embodiment. In this illustration, first input valve 324 and first output valve 326 are placed into a closed position.

As depicted, gas 332 only flows through main line 334 as shown by arrow 360. Gas 332 no longer flows through chamber 305. However, a sample of gas 332 is present in chamber 305. In this configuration of interface 304, a sample of gas 332 in chamber 305 is isolated from the flow of gas 332 as indicated by arrow 360.

Figure 9:
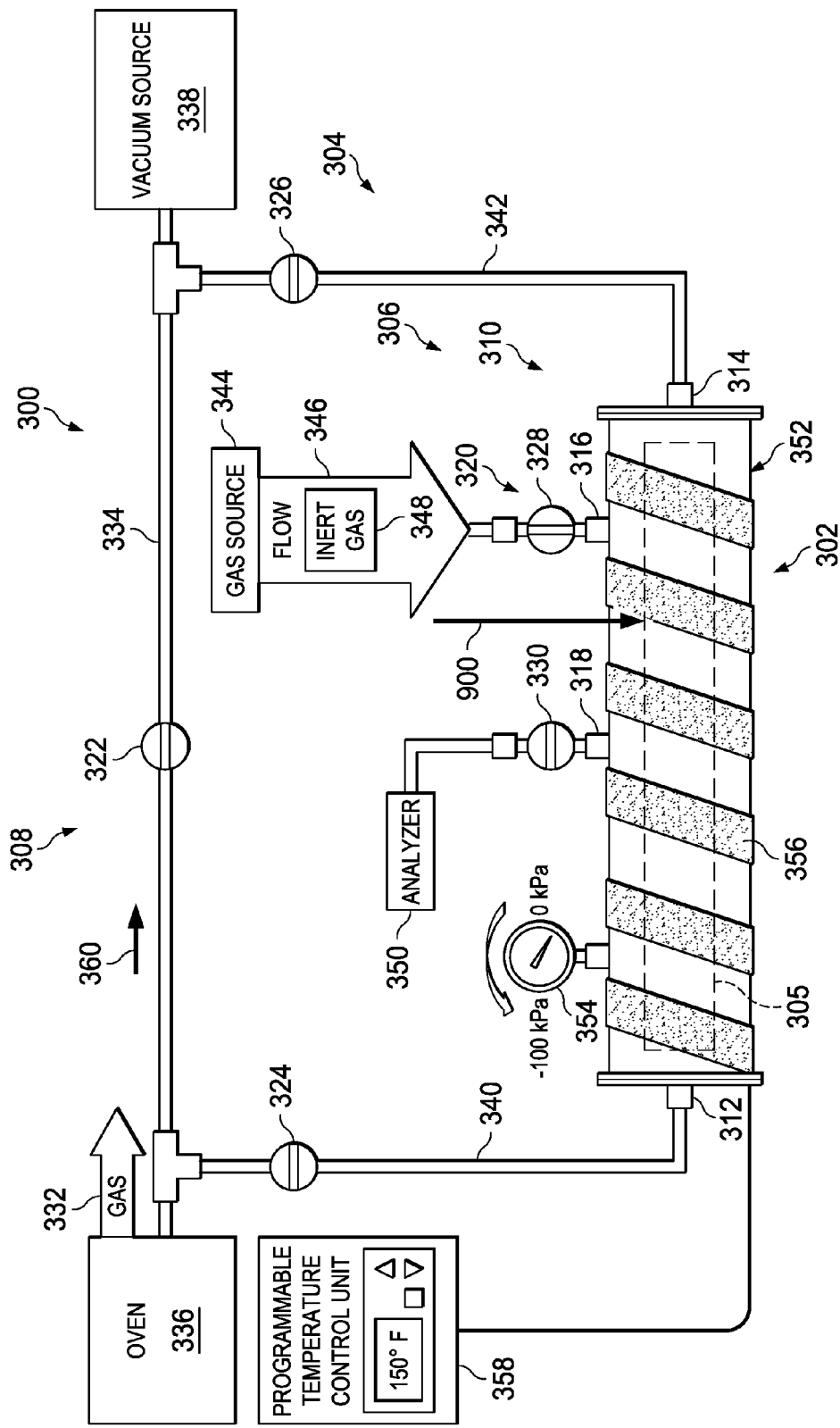

Turning now to FIG. 9, an illustration of another configuration of an interface for collecting a sample of gas is depicted in accordance with an illustrative embodiment. In this illustration, second input valve 328 is placed into an open position. Inert gas 348 flows into chamber 305 in the direction of arrow 900. Inert gas 348, however, does not flow out of chamber 305 in this illustrative example.

In this position, chamber 305 now increases in pressure from the introduction of inert gas 348 into chamber 305. As a result, pressure sensor 354 may now read about 0 kPa. In this illustrative example, 0 kPa is about 1 atmosphere.

Figure 10:
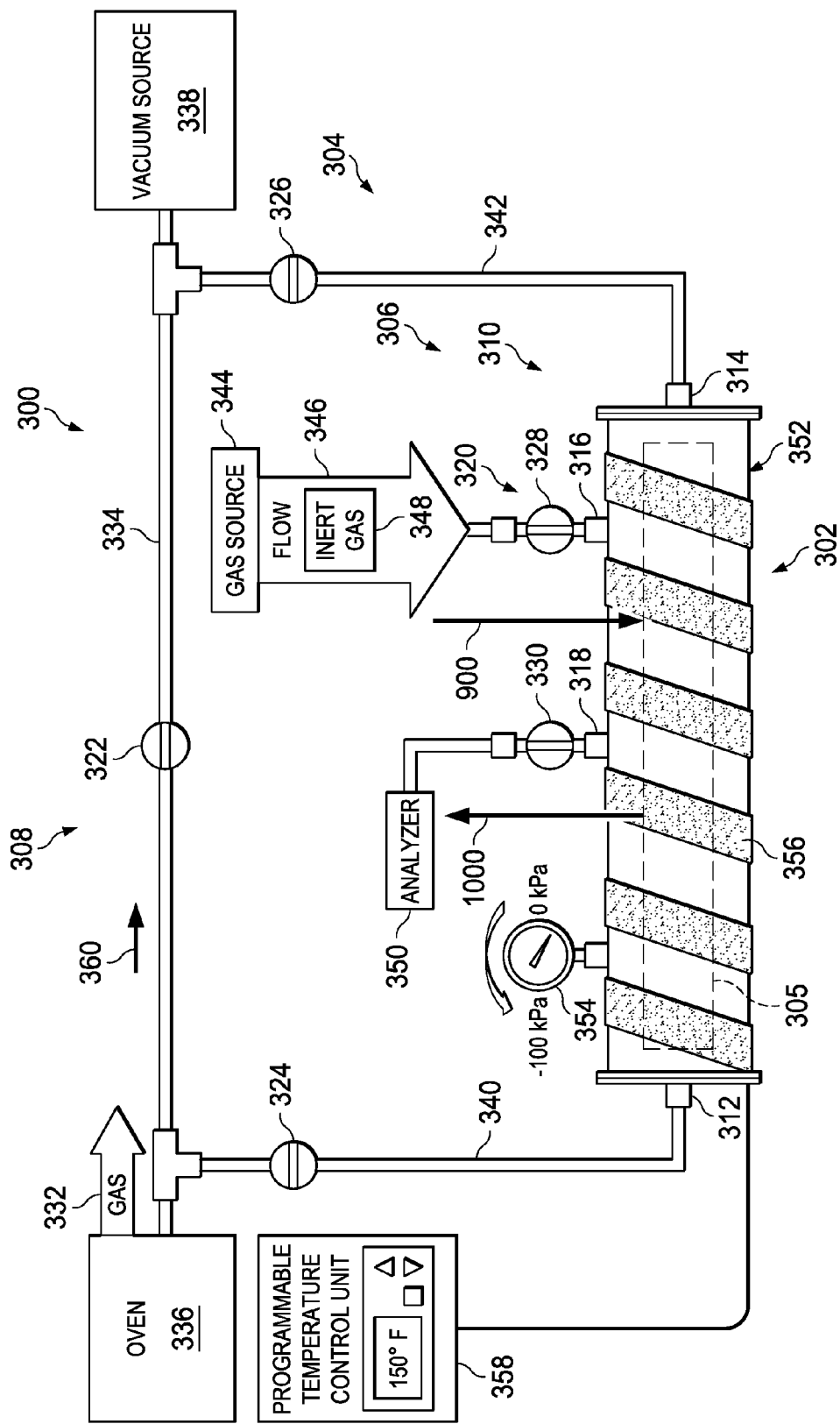

With reference now to FIG. 10, an illustration of another configuration of an interface for collecting a sample of gas is depicted in accordance with an illustrative embodiment. In this configuration, second output valve 330 is placed into an open position. With both second input valve 328 and second output valve 330 in the open position, inert gas 348 continues to flow into chamber 305 as shown by arrow 900. Additionally, inert gas 348 along with the sample of gas 332 flow out of chamber 305 to analyzer 350 as shown by arrow 1000.

In this manner, a collection of a sample of gas 332 may be made. Inert gas 348 may continue to flow into chamber 305 as shown by arrow 900, through chamber 305 and out of chamber 305 in the direction of arrow 1000. This flow may continue for a period of time to purge any remaining portions of gas 332 that may be present in chamber 305. At this point, gas sampling system 300 is ready to collect another sample of gas 332 in chamber 305.

Figure 11:
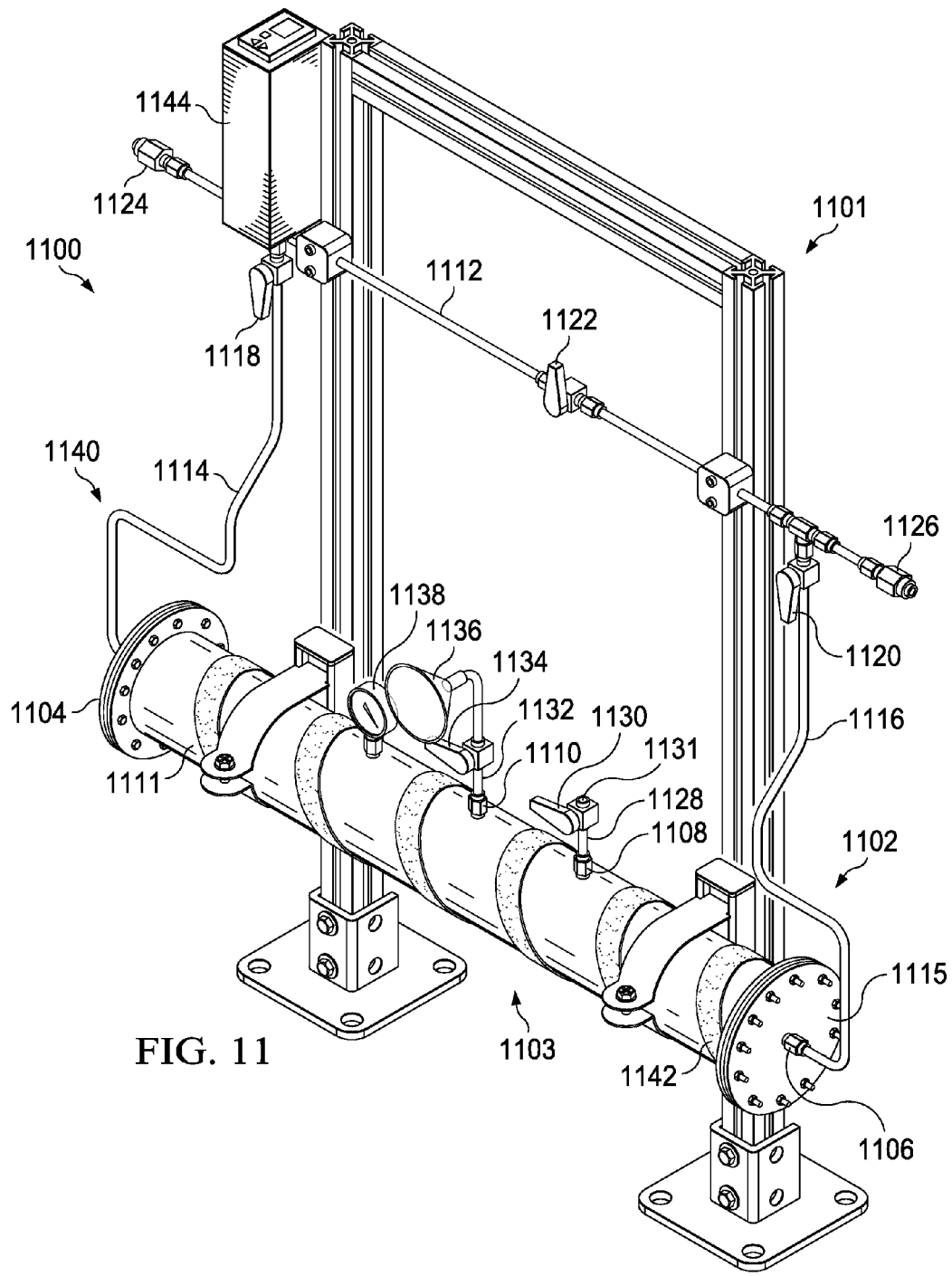
FIG. 11 is an illustration of a gas sampling system in accordance with an illustrative embodiment.

With reference now to FIG. 11, an illustration of a gas sampling system is depicted in accordance with an illustrative embodiment. Gas sampling system 1100 is an example of one physical implementation for gas sampling system 224 shown in block form in FIG. 2.

As illustrated, gas sampling system 1100 includes frame 1101, interface 1102, and sample collection structure 1103. The different components in interface 1102 and sample collection structure 1103 may be associated with frame 1101.

When one component is "associated" with another component, the association is a physical association in the depicted examples. For example, a first component may be considered to be associated with a second component by being secured to the second component, bonded to the second component, mounted to the second component, welded to the second component, fastened to the second component, and/or connected to the second component in some other suitable manner. The first component also may be connected to the second component using a third component. The first component may also be considered to be associated with the second component by being formed as part of and/or an extension of the second component.

Interface 1102 includes first input port 1104, first output port 1106, second input port 1108, and second output port 1110. First input port 1104 is located at end 1111 of sample collection structure 1103 and is connected to main line 1112 by line 1114. First output port 1106 is located at end 1115 of sample collection structure 1103 and is connected to main line 1112 by line 1116.

First input valve 1118 is located in line 1114. First output valve 1120 is located in line 1116. Main line valve 1122 is located in main line 1112. In this illustrative example, main line 1112 has connector 1124. Connector 1124 is configured to be connected to a vacuum line from a curing system. Main line 1112 also has connector 1126. Connector 1126 is configured to be connected to a vacuum line for a vacuum source.

Second input port 1108 is connected to line 1128. Second input valve 1130 is located on line 1128. Line 1128 has connector 1131. Connector 1131 is configured to be connected to an inert gas source.

Second output port 1110 is connected to line 1132. Second output valve 1134 is located on line 1132. Line 1132 includes connector 1136. Connector 1136 is configured to be connected to a line leading to an analyzer.

In this illustrative example, gas sampling system 1100 also includes pressure sensor 1138. Pressure sensor 1138 is configured to display a pressure in the chamber within sample collection structure 1103.

Gas sampling system 1100 also includes heating system 1140. Heating system 1140 includes heating elements 1142 and temperature control unit 1144. Temperature control unit 1144 may be a programmable temperature control unit in these illustrative examples.

As depicted, sample collection structure 1103 may have a cylindrical shape. For example, sample collection structure 1103 may be formed from a stainless steel pipe having a diameter of about 3 inches and a length of about 24 inches.

The other components such as the different lines in interface 1102 may be made of stainless steel tubing. Of course, other materials may be used in addition to or in place of stainless steel. For example, without limitation, the different materials may be selected from at least one of titanium, polyether ether ketone (PEEK), polycarbonate, and other suitable materials. The materials selected for use in interface 1102 and sample collection structure 1103 may be any material that may allow for a sample of gas to be collected without introducing contaminants. Further, the materials also may be selected as ones that do not corrode or wear more than desired through the collection of gas samples.

Of course, in other illustrative embodiments, wear and corrosion may not be a factor in the design of gas sampling system 1100. For example, one or more components in gas sampling system 1100 may be designed for a one time use. For example, sample collection structure 1103 may be used only once and replaced with another sample collection structure. As a result, contamination that may be caused within the chamber by the sample of gas collected in the chamber may not be of concern.

The illustrations of gas sampling system 300 in FIGS. 3-10 and gas sampling system 1100 in FIG. 11 are only illustrations of some implementations for gas sampling system 224 in FIG. 2. Other gas sampling systems may be implemented in different configurations and may have other components in place of or in addition to the ones illustrated in the figures.

For example, second output port 318 in gas sampling system 300 and second output port 1110 in gas sampling system 1100 may not be directly connected to an analyzer. Instead, the gas may be collected in a container that may then be connected to the analyzer.

As illustrated, the valves may be placed into different positions by a human operator. In yet another illustrative example, the different valves shown may be placed into different positions through a controller that may take the form of a hardware system such as a computer, an integrated circuit system, or some other type of hardware device. The controller may send signals to actuators associated with the valves to control the positions of the valves.

Figure 12:
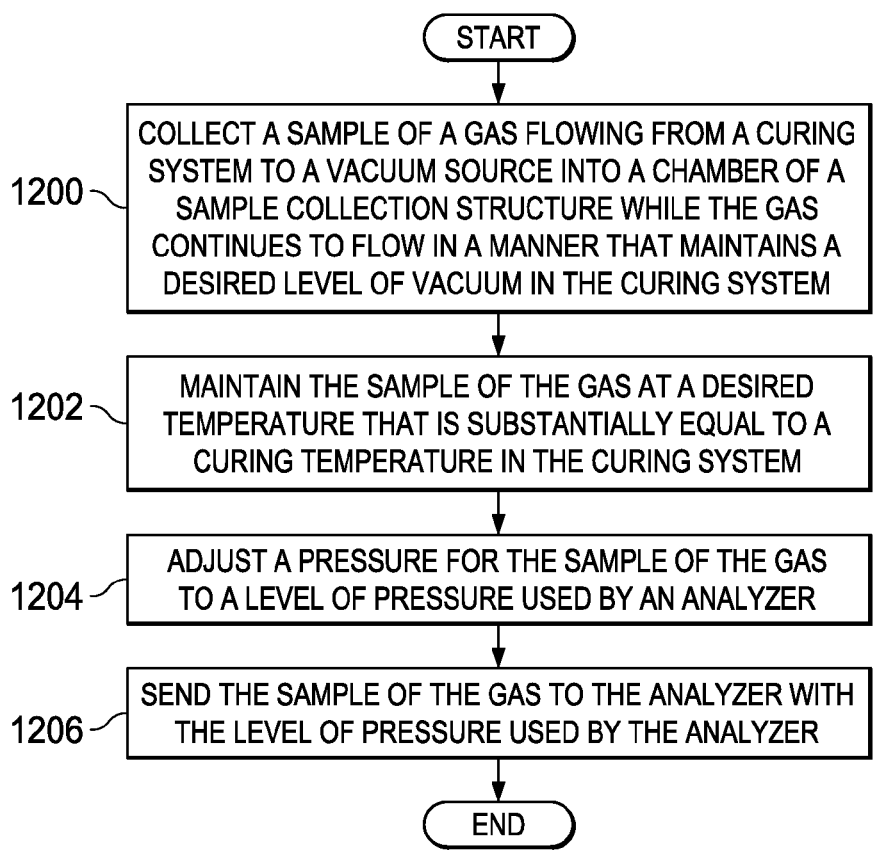
FIG. 12 is an illustration of a flowchart of a process for collecting a sample of a gas in accordance with an illustrative embodiment.

With reference now to FIG. 12, an illustration of a flowchart of a process for collecting a sample of a gas is depicted in accordance with an illustrative embodiment. The process illustrated in FIG. 12 may be implemented in composite part manufacturing environment 200 in FIG. 2. In particular, this process may be implemented using gas sampling system 224 in FIG. 2.

The process begins by collecting a sample of a gas flowing from a curing system to a vacuum source into a chamber of a sample collection structure while the gas continues to flow in a manner that maintains a desired level of vacuum in the curing system (operation 1200). The gas is generated from curing layers of composite material for a composite part in the curing system. The vacuum may be applied to a part or all of the composite part being cured in the curing system.

Next, the process maintains the sample of the gas at a temperature that is substantially equal to a curing temperature in the curing system (operation 1202). The process then adjusts a pressure for the sample of the gas to a level of pressure used by an analyzer (operation 1204). The sample of the gas is then sent to the analyzer with the level of pressure used by the analyzer (operation 1206), with the process terminating thereafter.

Figure 13:
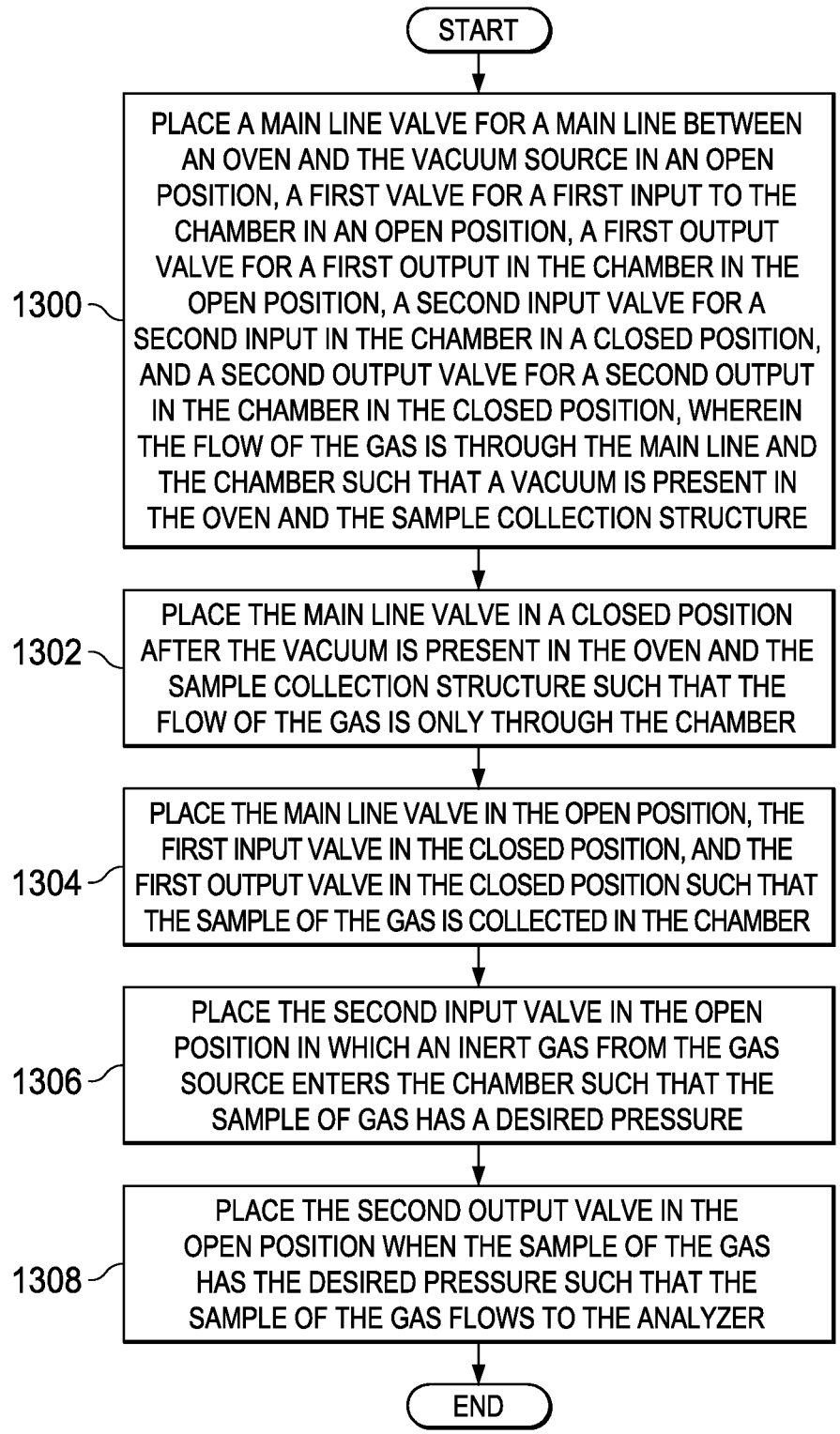
FIG. 13 is an illustration of a flowchart of a process for collecting a sample of gas flowing from a curing system to a vacuum source in a chamber of a gas sampling system in accordance with an illustrative embodiment.

With reference now to FIG. 13, an illustration of a flowchart of a process for collecting a sample of gas flowing from a curing system to a vacuum source in a chamber of a gas sampling system is depicted in accordance with an illustrative embodiment. The process illustrated in FIG. 13 is an example of one implementation for operation 1200 in FIG. 12. More particularly, the different operations illustrated in FIG. 13 may be implemented using a gas sampling system such as the diagram of gas sampling system 300 in FIGS. 3-10.

The process begins by placing a main line valve for a main line between an oven and the vacuum source in an open position, a first valve for a first input to the chamber in an open position, a first output valve for a first output in the chamber in an open position, a second input valve for a second input in the chamber in a closed position, and a second output valve for a second output in the chamber in a closed position, wherein the flow of the gas is through the main line and the chamber such that a vacuum is present in the oven and the sample collection structure (operation 1300). In operation 1300, the gas flows through both the main line and the chamber in the sample collection structure. In this manner, a sample of the gas may flow through the chamber.

The process then places the main line valve in a closed position after the vacuum is present in the oven and the sample collection structure such that the flow of the gas is only through the chamber (operation 1302). The process then places the main line valve in the open position, the first input valve in the closed position, and the first output valve in the closed position such that the sample of the gas is collected in the chamber (operation 1304).

Next, the second input valve is placed in the open position in which an inert gas from a gas source enters the chamber such that the sample of the gas has a desired pressure (operation 1306). The process then places the second output valve in the open position when the sample of the gas has the desired pressure such that the sample of the gas flows to the analyzer (operation 1308), with the process terminating thereafter.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

For example, in some illustrative examples, maintaining a curing temperature in operation 1202 may be omitted. As another example, operation 1202 and operation 1204 may be performed at substantially the same time.

Figure 14:
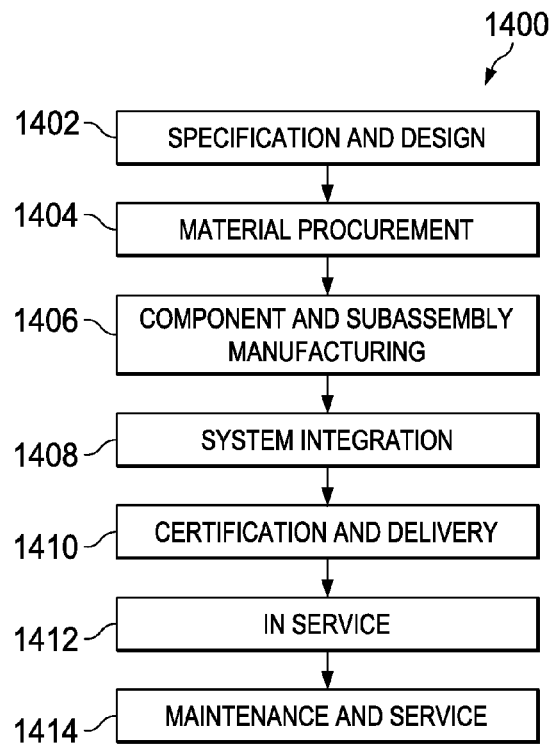
FIG. 14 is an illustration of an aircraft manufacturing and service method in accordance with an illustrative embodiment.
Figure 15:
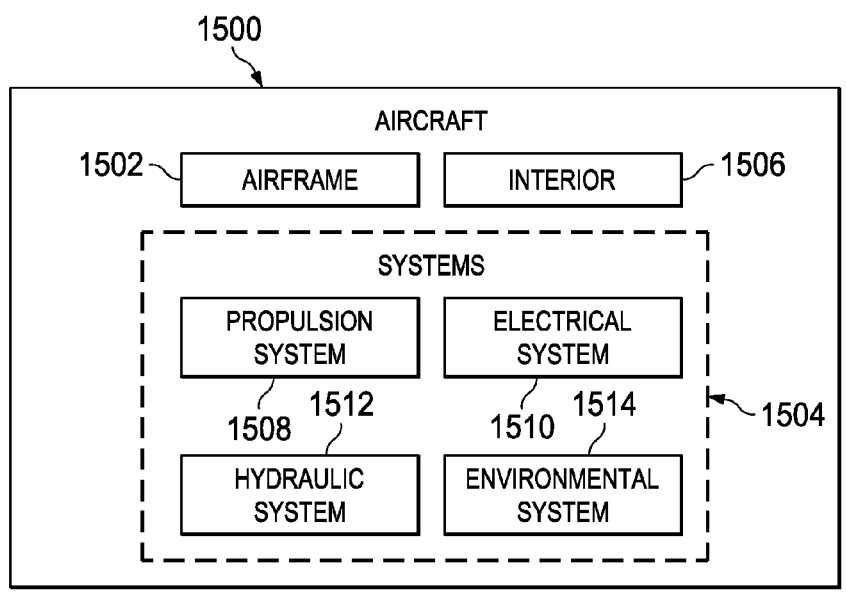
FIG. 15 is an illustration of an aircraft in which an illustrative embodiment may be implemented.

Illustrative embodiments of the disclosure may be described in the context of aircraft manufacturing and service method 1400 as shown in FIG. 14 and aircraft 1500 as shown in FIG. 15. Curing of composite parts, such as composite part 202, may be performing during aircraft manufacturing and service method 1400 and placed in aircraft 1500.

Turning first to FIG. 14, an illustration of an aircraft manufacturing and service method is depicted in accordance with an illustrative embodiment. During pre-production, aircraft manufacturing and service method 1400 may include specification and design 1402 of aircraft 1500 in FIG. 15 and material procurement 1404.

During production, component and subassembly manufacturing 1406 and system integration 1408 of aircraft 1500 in FIG. 15 takes place. Thereafter, aircraft 1500 in FIG. 15 may go through certification and delivery 1410 in order to be placed in service 1412. While in service 1412 by a customer, aircraft 1500 in FIG. 15 is scheduled for routine maintenance and service 1414, which may include modification, reconfiguration, refurbishment, and other maintenance or service.

Each of the processes of aircraft manufacturing and service method 1400 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 15, an illustration of an aircraft is depicted in which an illustrative embodiment may be implemented. In this example, aircraft 1500 is produced by aircraft manufacturing and service method 1400 in FIG. 14 and may include airframe 1502 with plurality of systems 1504 and interior 1506. Examples of systems 1504 include one or more of propulsion system 1508, electrical system 1510, hydraulic system 1512, and environmental system 1514. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1400 in FIG. 14. In one illustrative example, components or subassemblies produced in component and subassembly manufacturing 1406 in FIG. 14 may be fabricated or manufactured in a manner similar to components or subassemblies produced while aircraft 1500 is in service 1412 in FIG. 14.

One or more illustrative embodiments may be used to collect gas samples during the manufacturing of composite parts that may occur during various stages of manufacturing and service method 1400. For example, the illustrative embodiments may be used during component and subassembly manufacturing 1406, maintenance and service 1414 in FIG. 14, or during other stages.

The use of a number of the different illustrative embodiments may substantially expedite the assembly of and/or reduce the cost of aircraft 1500. For example, the results from the analyzer may be used to identify changes that may be made to a curing profile used to cure the composite part. As an example, a sample of the gas may be associated with the temperature and time during which the sample is collected in the curing process. Adjustments to the temperature and time may be made based on the components identified in the sample of gas.

Further, depending on the speed at which the analyzer is capable of generating results, adjustments to the curing profile may be made dynamically while the composite part is still being cured in the curing system.

The description of the different illustrative embodiments has been presented for purposes of illustration and description, and is not intended to be exhaustive or limited to the embodiments in the form disclosed. For example, although the illustrative examples for an illustrative embodiment are described with respect to composite parts for an aircraft, an illustrative embodiment may be applied to composite parts for other types of platforms. The platform may be, for example, a mobile platform, a stationary platform, a land-based structure, an aquatic-based structure, and a space-based structure. More specifically, the platform may be a surface ship, a tank, a personnel carrier, a train, a spacecraft, a space station, a satellite, a submarine, an automobile, a power plant, a bridge, a dam, a manufacturing facility, a building, and other suitable objects.

Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
    a sample collection structure having a chamber; and
    an interface for the sample collection structure, wherein the interface is configured to:
        be connected to a curing system configured to cure a composite part and a vacuum source configured to create a vacuum in the curing system,
        collect a sample of a gas from the curing system in the chamber, and
        send the sample of the gas collected in the chamber to an analyzer;
    the interface further comprising:
        an input port configured to be connected to a gas source; and
        an output port configured to be connected to the analyzer; and
    a valve system to collect the sample of the gas in the chamber and send the sample of the gas to the analyzer while the vacuum source maintains a desired level of vacuum in the curing system, the valve system comprising:
        an input valve configured to control a flow of an inert gas from the gas source to the second input port; and
        an output valve configured to control the flow of the inert gas from the second output port.

2. The apparatus of claim 1, wherein the interface is configured to send the sample of the gas collected with a desired pressure used by the analyzer.

3. The apparatus of claim 2, wherein the desired pressure is about one atmosphere.

4. The apparatus of claim 1, wherein the interface is configured to maintain a desired temperature for the sample of the gas.

5. The apparatus of claim 4, wherein the desired temperature is substantially equal to a curing temperature in the curing system.

6. The apparatus of claim 1, wherein the valve system is configured to control a flow of the gas between the curing system, the chamber, the vacuum source, and the analyzer.

7. The apparatus of claim 6,
    wherein, the input valve is a second input valve, the output valve is a second output valve, the input port is a second input port, and the output port is a second output port; and
    wherein the interface further comprises:
        a first input port configured to be connected to the curing system for the composite part;
        a first output port configured to be connected to the vacuum source; and
        a main line connecting the curing system to the vacuum source,
        wherein the valve system comprises:
            a main line valve configured to control the flow of the gas in the main line between the curing system and the vacuum source;
            a first input valve configured to control the flow of the gas from the main line to the first input port; and
            a first output valve configured to control the flow of the gas from the first output port to the main line.

8. The apparatus of claim 7, wherein a controller is configured to place the main line valve in an open position, the first input valve in a closed position, the first output valve in the closed position, the second input valve in the closed position, and the second output valve in the closed position when the sample of the gas is not needed.

9. The apparatus of claim 7, wherein a controller is configured to:
    place the main line valve in an open position, the first input valve in the open position, the first output valve in the open position, the second input valve in a closed position, and the second output valve in the closed position, wherein the flow of the gas is through the main line and the chamber such that the vacuum is present in the curing system and the sample collection structure;
    place the main line valve in the closed position after the vacuum is present in the curing system and the sample collection structure, wherein the flow of the gas is only through the chamber; and
    place the main line valve in the open position, the first input valve in the closed position, and the first output valve in the closed position, wherein the sample of the gas is collected in the chamber.

10. The apparatus of claim 9, wherein the controller is further configured to place the second input valve in the open position, wherein the inert gas from the gas source enters the chamber such that the sample of the gas has a desired pressure; and place the second output valve in the open position when the sample of the gas has the desired pressure such that the sample of the gas flows to the analyzer.

11. An apparatus comprising:
    a sample collection structure having a chamber, a first input port, a first output port, a second input port, and a second output port, wherein the first input port is configured to be connected to a curing system for curing layers of composite material for a composite part; the first output port is configured to be connected to a vacuum source; the second input port is configured to be connected to a gas source; and the second output port is configured to be connected to an analyzer; and a valve system associated with the first input port, the first output port, the second input port, and the second output port, wherein the valve system is configured to collect a sample of a gas from the curing system in the chamber and send the sample of the gas collected in the chamber to the analyzer; and wherein the valve system comprises:
an input valve configured to control a flow of an inert gas from the gas source to the second input port; and
an output valve configured to control the flow of the inert gas from the second output port.

12. The apparatus of claim 11, wherein the valve system is configured to collect the sample of the gas and send the sample of the gas to the analyzer while substantially maintaining a vacuum for the curing system.

13. The apparatus of claim 11 further comprising:
a heating system configured to maintain the sample of the gas at a desired temperature that is substantially equal to a curing temperature in the curing system.

14. A method for collecting a sample of a gas, the method comprising:
collecting, via an interface, the sample of the gas flowing from a curing system to a vacuum source into a chamber of a sample collection structure while the gas continues to flow in a manner that maintains a desired level of vacuum in the curing system, wherein the gas is generated from curing layers of composite material for a composite part in the curing system;
sending, via an interface, the sample of the gas to an analyzer with a level of pressure used by the analyzer;
collecting, via a valve system, the sample of the gas in the chamber; and
sending, via the valve system, the sample of the gas to the analyzer while the vacuum source maintains a desired level of vacuum in the curing system,
wherein the interface further comprises:
an input port configured to be connected to a gas source, and
an output port configured to be connected to the analyzer; and
wherein the valve system comprises:
an input valve configured to control a flow of an inert gas from the gas source to the input port, and
an output valve configured to control the flow of the inert gas from the output port.

15. The method of claim 14 further comprising:
analyzing the sample of the gas using the analyzer.

16. The method of claim 14 further comprising:
maintaining the sample of the gas at a desired temperature that is substantially equal to a curing temperature in the curing system.

17. The method of claim 14,
wherein the input port is a second input port, the input valve is a second input valve, the output port is a second output port, the output valve is a second output valve; and
wherein collecting the sample of the gas flowing from the curing system to the vacuum source into the chamber of the sample collection structure while the gas continues to flow in the manner that maintains the desired level of vacuum in the curing system comprises:
placing a main line valve for a main line between the curing system and the vacuum source in an open position, a first input valve for a first input port to the chamber in the open position, a first output valve for a first output port to the chamber in the open position, the second input valve for the second input port to the chamber in a closed position, and the second output valve for the second output port to the chamber in the closed position, wherein the flow of the gas is through the main line and the chamber such that a vacuum is present in the curing system and the sample collection structure;
placing the main line valve in the closed position after the vacuum is present in the curing system and the sample collection structure, wherein the flow of the gas is only through the chamber; and
placing the main line valve in the open position, the first input valve in the closed position, and the first output valve in the closed position, wherein the sample of the gas is collected in the chamber.

18. The method of claim 17 further comprising:
placing the second input valve in the open position, wherein the inert gas from the gas source enters the chamber such that the sample of the gas has a desired pressure; and
placing the second output valve in the open position when the sample of the gas has the desired pressure such that the sample of the gas flows to the analyzer.

19. The method of claim 14 further comprising:
adjusting a curing profile for use in forming the composite part.

* * * * *